United States Patent [19]
Carter et al.

[11] Patent Number: 5,288,462
[45] Date of Patent: Feb. 22, 1994

[54] STERILIZATION APPARATUS AND METHOD

[75] Inventors: Stephen D. Carter, Stone Mountain; James W. Brazell, Atlanta, both of Ga.

[73] Assignee: Stephen D. Carter, Stone Mountain, Ga.

[21] Appl. No.: 885,661

[22] Filed: May 18, 1992

[51] Int. Cl.$^5$ .............................................. H61L 2/00
[52] U.S. Cl. ....................................... 422/39; 422/112; 422/113; 422/114; 422/115; 422/292; 422/293; 422/294; 422/295; 137/535; 137/540
[58] Field of Search ..................... 422/33, 39, 112-115, 422/292-295; 137/535, 540

[56] References Cited

U.S. PATENT DOCUMENTS

| | | | |
|---|---|---|---|
| 1,711,097 | 4/1929 | Kratzer | 422/39 X |
| 1,728,333 | 9/1929 | Crowther | 422/39 X |
| 1,728,334 | 9/1929 | Crowther | 422/39 X |
| 3,415,613 | 12/1968 | Wallden | 422/295 X |
| 3,617,178 | 11/1971 | Clouston | 422/33 X |
| 3,627,209 | 12/1971 | Scott | 239/533 |
| 3,913,614 | 10/1975 | Speck | 137/543.19 |
| 3,944,387 | 3/1976 | Schreckendgust | 422/295 X |
| 4,226,642 | 10/1980 | Baran | 134/10 |
| 4,241,010 | 12/1980 | Baran | 422/2 |
| 4,543,987 | 10/1985 | Ekeleme, Jr. et al. | 137/540 |
| 4,748,003 | 5/1988 | Riley | 422/112 |
| 4,944,919 | 7/1990 | Powell | 422/26 |
| 4,973,449 | 11/1990 | Kolstad et al. | 422/27 |

FOREIGN PATENT DOCUMENTS

| | | | |
|---|---|---|---|
| 40887 | 12/1981 | European Pat. Off. | 422/39 |
| 3445990 | 6/1986 | Fed. Rep. of Germany | 422/39 |
| 2190993 | 12/1987 | United Kingdom | 137/535 |

OTHER PUBLICATIONS

"Pressure Inactivation of Microorganisms at Moderate Temperatures," Butz and Ludwig, Physica 139 & 140B (1986), pp. 875-877.

"Antimicrobial Effect of Water-Soluble Chistosans With High Hydrostatic Pressure," Papineau, Hoover, Knorr, and Farkas, Food Biotechnology, 5(1) 1991, pp. 45-57.

Primary Examiner—Robert J. Warden
Assistant Examiner—Krisanne M. Thornton
Attorney, Agent, or Firm—Hopkins & Thomas

[57] ABSTRACT

A sterilization apparatus has a chamber within a housing in which the materials to be sterilized are placed and the chamber is supplied with liquid under pressure. A pressure sensitive, rapid acting implosion cartridge is in communication with the chamber and acts to depressurize the chamber in milliseconds when the desired sterilization pressure is reached. The cartridge then reseals the chamber for a subsequent pressure build-up.

35 Claims, 5 Drawing Sheets

STERILIZATION APPARATUS AND METHOD

FIELD OF THE INVENTION

This invention relates to an apparatus and method for the pressure sterilization treating of various devices or materials, and, more particularly, to subjecting devices or materials to high pressure and rapid decompression to facilitate sterilization.

BACKGROUND OF THE INVENTION

Pressure treatment of various materials or devices, such as, for example, medical or dental instruments, in order to sterilize them has been used as an alternative to more common high temperature sterilization, such as steam sterilization, or high temperature washing. Steam sterilization generally requires an autoclave in which the instruments to be sterilized are placed, and a means for supplying steam to the autoclave. Such an arrangement is shown, for example, in U.S. Pat. No. 3,415,613 of Wallden. One of the disadvantages to such an arrangement is the danger inherent in using steam, which necessitates the use of expensive valving and steam conduit to minimize the possibility of leaks and accidental discharge of the steam.

Another type of sterilization process is liquid chemical sterilization, which requires a post treatment rinsing step, with the concomitant danger of recontamination, and gaseous disinfecting, such as with formaldehyde gas, which normally also requires an elevated temperature. In U.S. Pat. No. 4,973,449 of Kolstad et al. there is shown a method and apparatus for sterilizing dental instruments, for example, in which the instruments to be sterilized are placed in a sterilizing chamber and then subjected to relatively low and relatively high pressures in the presence of a sporicide atmosphere, which may comprise a mixture of formaldehyde, alcohol and water vapors, at a temperature in the range of 120° F. to 160° F. With the instruments in the chamber, the pressure in which is near a vacuum, a pressure pulse of vapor is introduced therein, the pressure being in the range of 25 psi to 40 psi above the starting pressure, and then the pressure is reduced to approximately the starting pressure. A preferred rate of pulsing is given as twenty discrete pulses within a two minute pulsing period. The actual sterilization depends on the sporicidal atmosphere, and the pulsing is alleged to enhance the effectiveness of that atmosphere. In addition, the process requires a relatively complex valving system to achieve the desired pulses.

Other sterilization arrangements use sterilization gas (U.S. Pat. No. 3,944,387 of Schreckendgust), and saturated steam (U.S. Pat. No. 4,944,919 of Powell).

The various prior art arrangements, which for the most part, depend upon heat (steam), radiation, or chemicals (formaldehyde vapor) are not practical where the material to be sterilized may consist, for example, of biomolecules, since desirable organisms may be destroyed along with undesirable organisms. Thus, it has been necessary to find alternative sterilization techniques, such as hydrostatic pressure sterilization, where the microorganisms are subjected to pressures as great as 3000 bar. Good experimental results in which unwanted microorganisms have been destroyed have been reported, but no definitive structure or system apparently has been proposed. See, for example, "Pressure Inactivation of Microorganisms at Moderate Temperatures" by P. Butz and H. Ludwig, Physica 139 and 140B (1986), North-Holland, Amsterdam at pp. 875-877.

Thus, while purely hydrostatic pressure treatment eliminates the dependence on high temperatures and/or chemical vapors for sterilization, with their attendant handling problems, the factors of versatility, convenience, economy, and simplicity have not been adequately addressed, nor have the pressures used nor the pressure redirection rates been sufficiently great to accomplish complete sterilization.

SUMMARY OF THE INVENTION

The present invention is a method and apparatus for pressure treating materials and/or devices without the necessity of an elevated temperature or a sporicidal atmosphere, and the principles thereof are of special utility in the sterilization of medical and dental tools, although not limited to such uses. Literally any other device or instrument which itself would not be structurally, adversely affected could be subjected to the method of the present invention. In the illustrative embodiments of the invention, the principles thereof, however, are disclosed as applied to a method and apparatus for sterilizing dental tools.

The apparatus of the invention comprises a housing defining a pressure chamber therein which receives, for example, a stainless steel basket containing the instruments or tools to be sterilized. A pressure pump is connected to the chamber through suitable fluid transmission components, and is adapted to supply, under pressure, a fluid, such as air, gas or water, including demineralized or carbonated water, from a reservoir to the chamber.

Connected to the pressure chamber is a rapid opening valve which either may be operator controlled or automatically activated, or which is designed to open suddenly when the pressure within the chamber reaches a predetermined value, such as, for example, three to four thousand pounds per square inch in the case of air, vapor or other gas, or fifty-five thousand pounds per square inch in the case of water. The rapid opening of the valve produces an explosive decompression in the chamber, which effectively causes the microorganisms to, in a sense, explode or be highly stressed as to be killed, or inactivated. In other words, the pressure differential per unit time, in which the time is nearly instantaneous, stresses the microorganisms to the point of inactivation. Thus, the microorganisms, the inactivation of which is the principal function of the present invention, are subjected to two destructive phases. They are first subjected to high pressure deactivation, and then to an explosive decompression deactivation. By explosive decompression is meant the rapid removal of pressure from the pressure chamber within an elapsed time measured in milliseconds, such as, for example, one to ten milliseconds.

The rapid opening valve means of one embodiment of the invention comprises an implosion cartridge mounted in or adjacent to the pressure chamber. The cartridge comprises a housing defining an interior, cartridge chamber being in communication through a restricted inlet passageway with the pressure chamber containing the tools. A valve seat is formed by a first bore extending from a first portion, or as illustrated, the uppermost portion of the cartridge chamber to the inner end of the restricted inlet passageway. A spherical valve ball of slightly smaller diameter than the diameter of bore containing the ball, is located therein. The valve ball is supported against the inner opening of the restricted inlet passageway by a semi-flexible metal column having a first ball seating member on its end adjacent the restricted inlet passageway. A restraining collar is disposed within the cartridge chamber and held rigidly and immovably against the housing side wall. The restraining collar is aligned normal to the longitudinal axis of the chamber, and defines a central opening and a series of openings adjacent the central opening. The metal column extends preferably axially through the cartridge chamber from the first bore, through the central opening of the restraining collar, into a second bore at the opposite end of the cartridge housing, and terminates adjacent to a second ball. The second ball is supported between a second ball seating member attached to the opposite end of the metal column from the first ball seating member, and a longitudinally adjustable or third ball seating member. A purging channel or passageway connects the second bore and the cartridge chamber to the exterior of the implosion cartridge. The purging passageway, in this embodiment of the invention, is connected exteriorly of the chamber housing to a conduit and valve arrangement for purging the cartridge of any accumulated fluid.

In a second embodiment of the invention, the implosion cartridge is mounted externally of the pressure chamber housing and is in communication therewith through a suitable communicating passageway. The remaining elements of the sterilization apparatus are essentially identical to those discussed above.

In the operation of either of the first two embodiments of the invention, with the tools to be sterilized placed in the pressure chamber, optionally using a basket to contain the tools, the pressure chamber is pressurized by the introduction of a high pressure flow of water or other suitable liquid. The first ball valve seals the inner opening of the restricted inlet passageway from the pressure chamber into the implosion cartridge until the critical buckling load of the column is reached. At this point, the column buckles substantially instantaneously to a controlled degree, thereby removing the ball valve from the inner opening, with a consequent passage of fluid under pressure through the inner opening of the restricted inlet passageway and into the first bore, producing an explosive depressurization of the pressure chamber. The degree of buckling of the column is controlled by the restraining collar, so that the column material is not stressed beyond its elastic limit. The restricted inlet passageway remains open until the pressure on the ball and, hence, on the column, reaches the column restoring threshold, at which time the column snaps back into its starting configuration, thereby causing the ball to seal the inner opening, and so the restricted passageway. Where several cycles of compression and decompression are desired, the fluid pump may run continuously, inasmuch as the pressure build-up takes much more time than the decompression portion of the cycle.

In a third embodiment of the present invention, a housing defining a pressure chamber is connected through suitable pressure lines to an air compressor. The tools or instruments to be sterilized are placed into the pressure chamber of the housing, and the air compressor is activated to pressurize the chamber to approximately 3000 psi. The microbes or organisms contaminating the instruments or tools are thus subjected to the chamber pressure. The pressure chamber also is in fluid communication with a quick opening valve capable of opening so quickly so as to allow nearly instantaneous depressurization of the pressure chamber. The compressed air is directed into a surge tank defining an expansion chamber, and thereafter is directed to a muffler. The microorganisms contaminating the tools are therefore subjected to pressurization and thereafter to nearly instantaneous depressurization, occurring within approximately 1 to 10 milliseconds. In this and the other embodiments of the invention disclosed herein, repetitive cycles of pressurization and depressurization can be utilized to subject the tools and their associated contaminants to repetitive cycles, as selectively desired.

The features and advantages of the present invention are readily apparent from the following detailed description, read in conjunction with the accompanying drawings.

DETAILED DESCRIPTION

Figure 1:
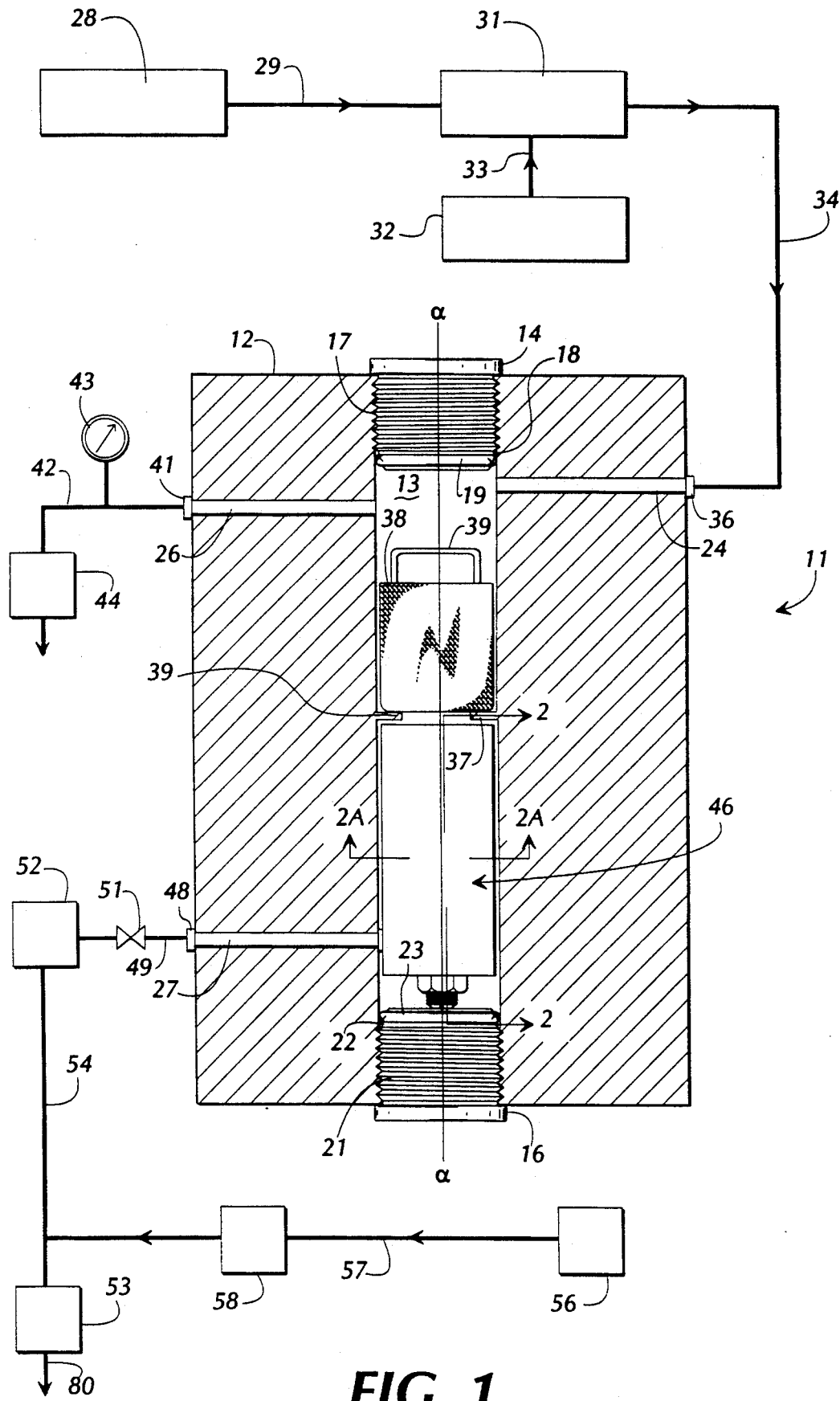
FIG. 1 is a side elevation, diagrammatic view of the sterilization apparatus of one embodiment of the present invention.
Figure 7:
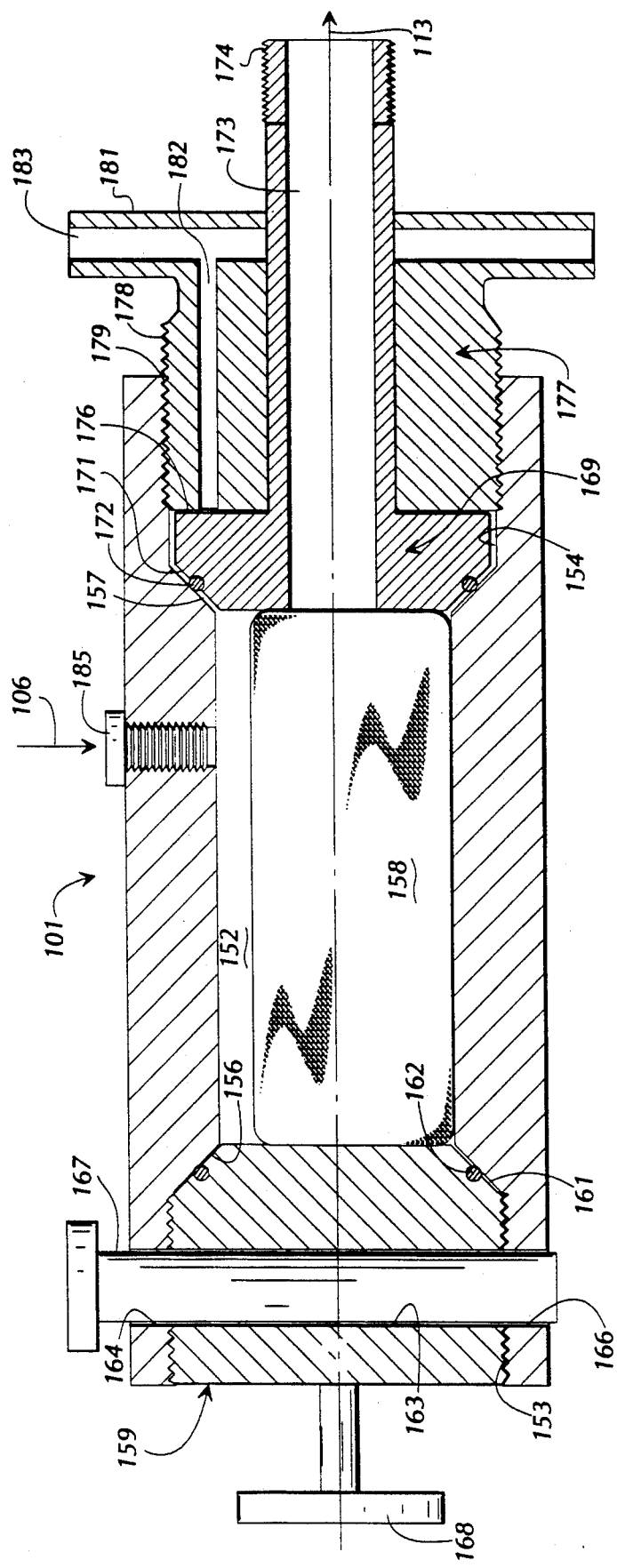
FIG. 7 is a sectional view of another form of pressure chamber for use with the apparatus of FIG. 6.

In FIG. 1 there is shown a sterilization apparatus 11 for the pressure treatment of, for example, dental tools. The apparatus 11 comprises a housing 12 of high strength steel or other suitable material capable of withstanding extremely high pressures, defining a pressure chamber 13 therein. Housing 12 and pressure chamber 13 are preferably cylindrical in shape, and, as depicted in FIG. 1, coaxial along longitudinal axis $a$; however, they may take other shapes as well. Chamber 13 is pressure sealed by means of threaded sealing plugs 14 and 16 at the top or first end and the bottom or second end, respectively, of housing 12. Alternatively, sealing plugs 14 and 16 also could be in the form of sealing plug 159 shown in FIG. 7 and discussed in detail below. It is to be understood that while the housing 12, and its associated components, are depicted as being vertically oriented in FIG. 1, thus having an upper and a lower end, such orientation is not necessary, inasmuch as virtually any orientation, including horizontal, of housing 12 is possible without impairment of the function of the apparatus 11. Sealing plug 14 has a threaded portion 17 which screws into matching threads at the top or first end of the housing, and a sealing portion 18 having a pressure sealing gasket 19 which seals the upper end of pressure chamber 13. In a like manner, plug 16 has a threaded portion 21, a sealing portion 22 and gasket 23 for sealing the opposite, or in this case, lower or second end of chamber 13. Chamber 13 communicates with the exterior of housing 12 through an input conduit 24 and an output conduit 26, and an input-output conduit 27.

Chamber 13 is intended to be pressurized by a fluid, such as, for example, demineralized water which may be carbonated for additional effect. A pump 28 delivers, via schematically depicted conduit 29, oil or suitable fluid under pressure of, for example, twelve thousand pounds per square inch (12 Kpsi) to a pressure intensifier 31 which is supplied with, for example, demineralized, carbonated water from a reservoir 32 via conduit 33. The output of intensifier 31 is water under a pressure of, for example, sixty thousand pounds per square inch (60 Kpsi) which is directed to pressure chamber 13 via a conduit 34, connecting fitting 36, and conduit 24. Within chamber 13 is a septum 37 which forms a shelf or buttress upon which a basket 38, having a handle 39 contacts. Basket 38 is preferably an open weave structure made of suitable material, such as stainless steel, and is adapted to receive loose dental tools or tools contained or sealed in bags or packages. Additional materials, such as stainless steel balls (not shown), can be added along with the tools in basket 38 so as to take up more volume of chamber 13, so that less volume of chamber 13 has to be pressurized. Septum 37 and basket 38 are not absolutely necessary, but they do facilitate insertion and removal of the tools to be sterilized, especially where, as in FIG. 1, the housing 12 is oriented vertically.

Connected to outlet passage or conduit 26 via a suitable coupling 41 is a conduit 42 having a pressure gauge 43 connected thereto, and a relief valve 44. Gauge 43 may contain a suitable controlling transducer which opens valve 44 when the pressure within chamber 13 exceeds a safe or otherwise desired maximum, in the case of the apparatus of FIG. 1, a pressure somewhat greater than the desired operating pressure of 55-60 Kpsi (thousand pounds per square inch). Alternatively, valve 44 itself may be set to open automatically when the safe or desired upper limit of pressure is attained. In practice, it is contemplated that the safe limits never will be exceeded, hence valve 44 is intended primarily as an emergency safety device. It is possible that the pressurizing portion of the cycle of the apparatus may, for various reasons, have to be interrupted. Valve 44 may include a manual actuating control to bleed off the pressure that has been built up prior to such interruption.

Chamber 13 also contains an implosion cartridge 46 which is depicted as resting on or contacting sealing plug 16 and which is connected via a suitable fitting 47 to passage or input/output conduit 27. Conduit 27 in turn is connected via a suitable fitting 48 to a conduit 49 having a two way valve 51 therein. Valve 51 is connected to a purge valve 52 which, in turn, is connected to a relief valve 53 through a conduit 54. An air compressor 56 is connected through a conduit 57 to a check valve 58, the output of which also is connected to conduit 54 between valves 52 and 53. As is described hereinafter, compressed air from compressor 56 is applied to a chamber defined by cartridge 46 through valves 58, conduit 54, valves 52 and 51, conduit 49 and conduit or passage 27 to purge it of residual fluid.

Figure 2:
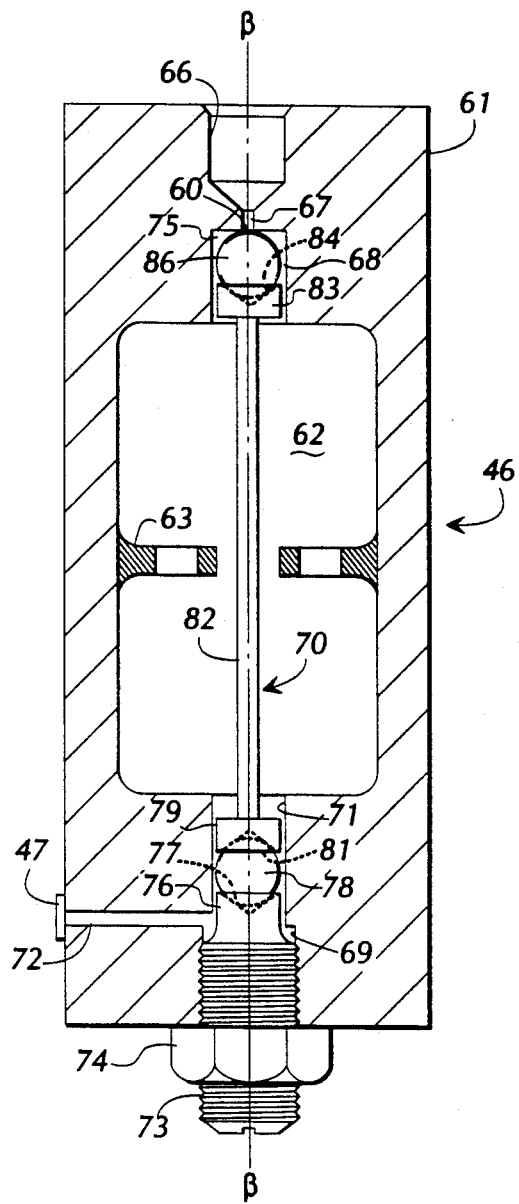
FIG. 2 is an elevation, cross-sectional view of an implosion cartridge for use in the apparatus of FIG. 1, taken along lines 2—2 of FIG. 1.
Figure 2A:
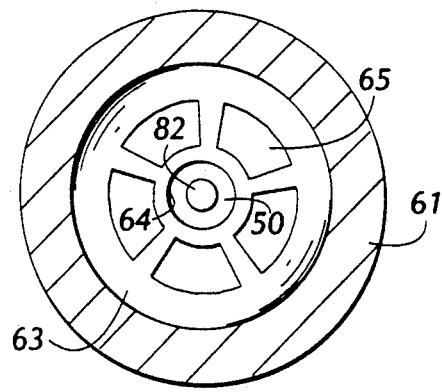
FIG. 2A is a cross-sectional view of the implosion cartridge taken along lines 2A—2A of FIG. 1, also showing a plan view of the restraining collar.

FIG. 2 depicts the implosion cartridge 46 of FIG. 1 which, in operation, provides for an explosive decompression of pressure chamber 13. Cartridge 46 comprises a housing 61 which is elongate along central longitudinal axis $\beta$ and formed of a material capable of withstanding high pressures, such as any of a number of steels or steel alloys. Since cartridge 46 preferably, but not absolutely, is received concentrically within pressure chamber 13 of housing 12, axes $\alpha$ and $\beta$ normally will be the same, and are so illustrated in the present description. Housing 61 defines therein interior, cartridge chamber 62. Restraining collar 63 is disposed across cartridge chamber 62 within and extending to opposing portions of the interior side wall of housing 61 as shown in FIG. 2A. Collar 63 is a rigid, ring-shaped member, and is itself rigidly held in place normal to the longitudinal axis $\beta$ of housing 61 by any suitable means (not shown), including welding, by fasteners such as metal screws or bolts or even by friction engagement. Collar 63 includes an annular, central, ringed side wall 64 which defines therethrough a central opening 50 concentrically aligned along axis $\beta$ of housing 61. Side openings 65 also are defined through collar 63 to provide, along with opening 50, fluid communication within cartridge chamber 62 on each side of collar 63, so that the pressure within chamber 62 is substantially equal on both sides of collar 63. Chamber 62 communicates with the exterior of housing 61 at a first end thereof through an opening 66, a restricted inlet passageway 67, and a bore 68. Restricted inlet passageway 67 terminates at its inner end at opening 60 defined by housing 61 at the upper end of bore 68 and shown in FIG. 2, so that fluid flowing through passageway 67 to bore 68 must pass through opening 60. The criticality of the cross-sectional area of opening 60, and hence passageway 67, is to ensure that ball 86 is sized larger than opening 60 to close passageway 67 when the ball is forced against the end of bore 68 which defines opening 60. The other or second end of housing 61 defines a threaded bore 69 therein communicating with another bore 71, which opens into chamber 62. Bore 71, and hence chamber 62 is in communication with the exterior of housing 61 through a passage or conduit 72, which is designed to couple to conduit 27 in housing 12 through fitting 47, as shown in FIG. 1. The shape and dimensions of bore 71 are not critical, and can be of any other shape and dimension which would allow for the flow of fluid from chamber 62 past ball 78 to conduit 72.

Within threaded bore 69 is an adjusting and support screw 73 which is locked in a selective position by a suitable lock nut 74. The end portion 76 of screw 73 is of reduced diameter to permit it to pass into bore 71 while spaced inwardly of the side wall of bore 71, and the distal end of end portion 76 has a cone-shaped recess 77 formed therein, as indicated by the dashed lines.

As discussed and shown in FIG. 2, housing 61 is preferably, although not necessarily, cylindrical in shape, and opening 66, passageway 67, and bores 68, 69, and 71 are cylindrical and axially aligned along the central, longitudinal axis $\beta$ of housing 61. It is to be understood the above-described embodiment is only illustrative of one shape of the present invention, and that other shapes of housing 61 and its associated elements can be used without departure from the features and principles of the invention.

The actuating mechanism 70 of cartridge 46 includes a first spherical ball 78 which rests against the surface of recess 77. Ball 78 has a diameter less than the diameter of bore 71 so as to permit passage of water or fluid between the side wall of bore 71 and ball 78, and is held against surface 77 by a ball retainer 79 which also has a cone-shaped recess 81 bearing against ball 78 opposite end portion 76. Retainer 79 is securely mounted to one end of a rod or column 82, which rod is comprised of a high strength material such as, for example, stainless steel. As will be apparent hereinafter, column 82 is of a material and size to exhibit a critical buckling load under axially directed compression, in the approximate range of 55-60 Kpsi applied against one end of column 82, that is against the projected area defined by opening 60.

Column 82 extends from ball retainer 79 through chamber 62, passing through central opening 50 of collar 63, and into bore 68, where it terminates in a second ball retainer 83 having a cone-shaped recess 84, as indicated by the dashed lines. A spherical ball or ball valve 86 rests in recess 84 and bears against the end of bore 68 defining opening 60, thereby blocking restricted passageway 67. Adjusting screw 73 is selectively rotated to adjust the force of column 82 against ball 86 so that ball 86 is firmly seated against the end of bore 68, thus completely covering opening 60. The diameter of ball 86 is slightly, for example a few millimeters, less than that of bore 68 in order that fluid under pressure may pass through opening 60 from restricted inlet passageway 67 to bore 68 and into chamber 62 when ball 86 moves away from its blocking position against the end of bore 68 and opening 60. The ball 86 acts as a piston to maintain column 82 in a buckled condition until the pressure is decreased in volumes 75 defined between ball 86 and the side wall of bore 68, to about 10 Kpsi. The distance between the side wall of bore 68 and ball 86, and/or the size of volume 75 can be selectively varied to change the reset time of actuating mechanism, as is discussed below.

In operation, with reference to FIGS. 1, 2, 2A, and 3, tools to be sterilized, either packaged or loose, are placed in basket 38 within chamber 13 in which cartridge 46 is inserted and connected, and chamber 13 is sealed with plug 14. Pump 28 working in conjunction with intensifier 31 deliver, for example, carbonated water under pressure to chamber 13 through inlet passage or conduit 24. The pressure in chamber 13 increases until a pressure of, for example, 55 Kpsi exists in chamber 13, thus subjecting the tools, and any microorganisms on the tools, to this high pressure. Rod or column 82 is designed, for example, to have a critical buckling load threshold corresponding to 55 Kpsi at opening 60 which is applied axially to the rod through passage or opening 66, restricted inlet passageway 67, opening 60 and against the portion of ball 86 which covers opening 60. It should be readily understood that since, at this point, ball 86 is blocking inlet passageway 67 by being forced against the end of bore 68 to cover opening 60, the pressure directed against ball 68 is applied directly against the area of ball 86 which covers opening 60. This area of ball 86 against which the pressure is applied at this point is less than the diametrical cross-sectional area of ball 86. It is characteristic of the critical load buckling phenomenon that the rod is straight just prior to the attainment of the corresponding threshold pressure, and then buckles substantially instantaneously at the threshold.

Figure 3:
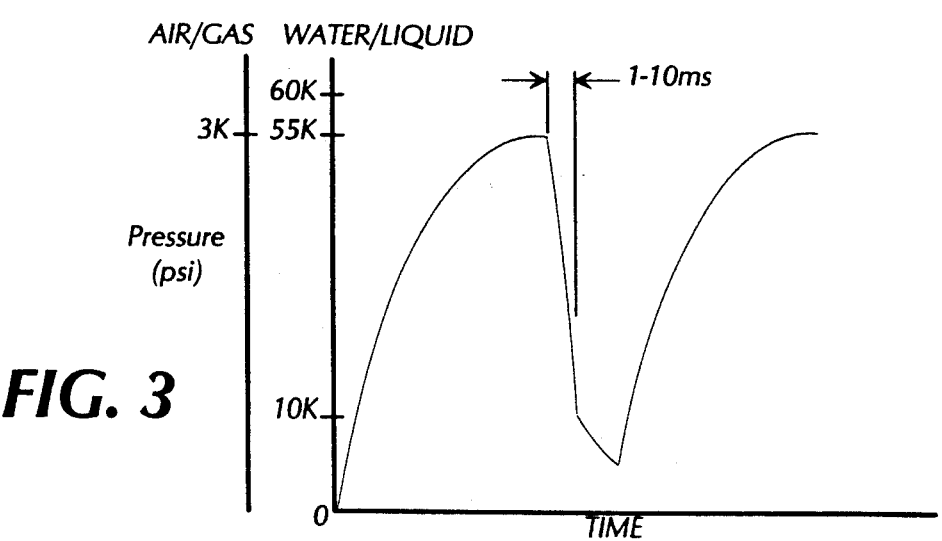
FIG. 3 is a graph of the pressure versus time cyclic relationship of the atmosphere within the pressure chamber.

With reference to FIG. 2, when the critical buckling load corresponding to a pressure of approximately 55 Kpsi is reached, column 82 buckles, ball 86 drops down from its blocking position over opening 60 at the upper end of bore 68, and water under pressure passes through inlet passageway 67, through opening 60 and into bore 68 to fill the volumes 75, shown in FIG. 2, which are defined between ball 86 and the upper end corners of bore 68. As fluid passes from inlet passageway 67 into volumes 75 of bore 68, the pressure in chamber 13 is substantially instantaneously reduced. For example, the pressure in chamber 13 can be reduced from 55 Kpsi to approximately 10 Kpsi in from one to ten milliseconds. Only a very small amount of water passes into volumes 75 before 10 Kpsi is reached, which is the restoring threshold for column 82. The pressure of the fluid in volumes 75 will hold ball 86 away from its closure position against the end of bore 68 over opening 60 for a period of time until enough fluid passes from volumes 75 past ball 86 and into chamber 62 so that the pressure in chamber 13 and the corresponding load against ball 86 becomes less than the restoring threshold for column 82. When the corresponding restoring threshold for column 82 is reached by the pressure of the fluid, column 82 snaps back into a straight alignment so that ball 86 again seals or blocks passageway 67. Thus, as shown in FIG. 3, chamber 13 and the objects within it have been subjected to a pressure build-up, and an explosive decompression. Chamber 62 is of a volume sufficiently larger than the amount of fluid displaced when column 82 buckles, allowing fluid into bore 68, that the pressure in chamber 13 is substantially reduced. For example, the volume of chamber 62 may be fifty to one hundred times greater than the volume of fluid substantially, instantaneously displaced into bore 68 when column 82 buckles.

FIG. 3 shows the curve characteristic for this pressure versus time process, with reference made to the "water/liquid" variable along the graph's y-axis. If desired, the pressure build-up and the decompression may be performed over several cycles, the build-up stage of a second cycle being shown in FIG. 3. In such cases, each cycle would be substantially identical to the pressurization/depressurization cycle shown in FIG. 3. Various columns having different buckling thresholds can be substituted for column 82 to alter the cyclic pressurization and depressurization in chamber 13.

The conical surfaces 77 and 84 maintain full contact with their respective spherical members 78 and 86 despite the angular movements of the ends of column 82 during buckling and restoration.

Adjusting screw 73 is used properly to seat ball 86 against the end of bore 68 adjacent opening 60 so that the fluid does not leak past ball 86 and into bore 68 until the critical buckling load is reached. Adjustment is made simply by pressurizing chamber 13, and checking the pressure gauges to determine if the chamber 13 is losing pressure at a given pressure setting. Plug or screw 73 is turned to apply more pressure against ball 86 to stop undesired leaking of fluid past ball 86.

In the operation as discussed, column 82 is prevented from buckling beyond a selected limit by ringed side wall 64 of restraining collar 63. The diameter of ringed side wall 64 can be selectively varied to allow for a greater or lesser buckling of column 82, as desired. In addition, the diameter of ball 86 relative to bore 68 is such that after column 82 buckles and fluid fills volumes 75, the fluid pressure will be maintained on ball 86, thereby keeping inlet passageway 67 open, until the column restoring threshold is reached. The operation of the apparatus of FIGS. 1 and 2 depends upon the fact that water, while generally regarded as incompressible, in actuality is compressible to a certain extent. The bulk modulus of elasticity of water is a finite number, i.e., less than infinite, hence the pressure elasticity which is proportional to the reciprocal of the bulk modulus of elasticity, is a real number, albeit quite small.

After the desired number of cycles of compression/decompression have been achieved, chamber 62 is purged of any remanent water therein. Air compressor 56 forces air under pressure into chamber 62 through conduits 27 and 72. After chamber 62 is air pressurized, check valve 58 is closed and relief valve 53 is thereafter opened, allowing the pressurized air in chamber 62 rapidly to escape through valves 51, 52, and 53, and outside of apparatus 11, through outlet conduit 80. Fluid within chamber 62 will be carried out of apparatus 11 through valves 51, 52, and 53 and conduit 80 along with the escaping air.

Figure 4:
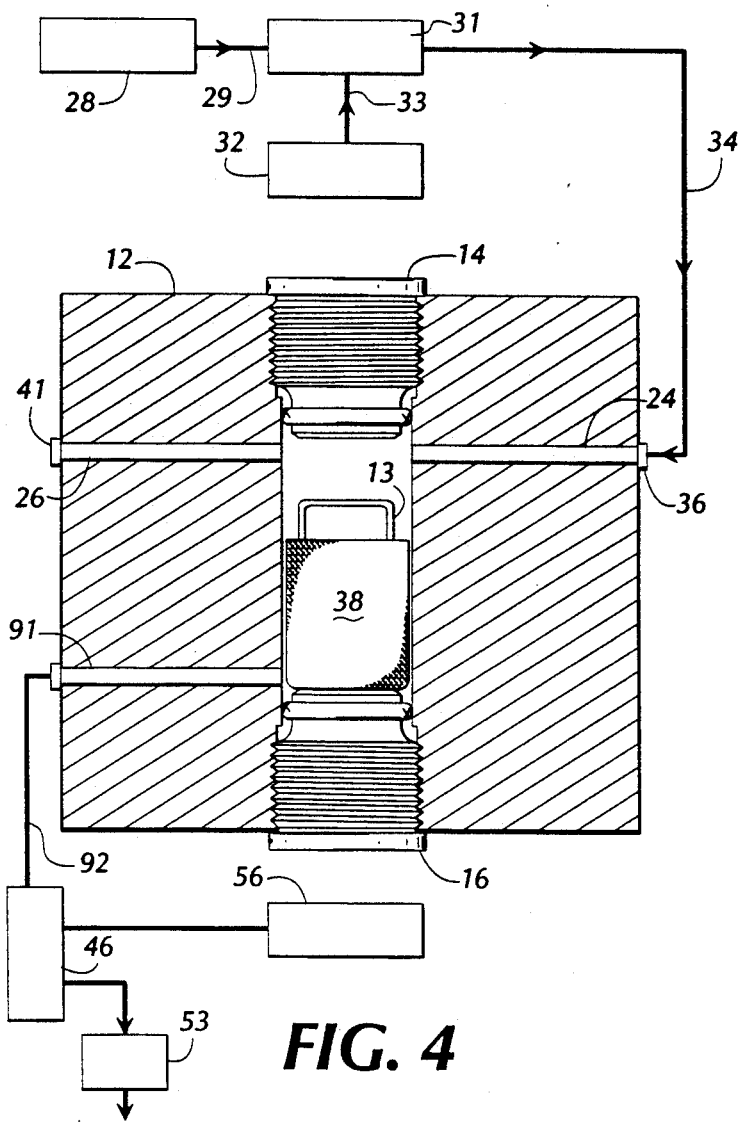
FIG. 4 is an elevation, diagrammatic view of a second sterilization apparatus embodying the principles of the present invention.

FIG. 4 depicts an apparatus similar to that of FIG. 1 and like parts bear the same reference numerals. In FIG. 4 the implosion cartridge 46 is external of the housing 12, and communicates with pressure chamber 13 through passageway 91 in housing 12, and through conduit 92. Such an arrangement adds a degree of flexibility in locating at least a portion of the apparatus 11 in a relatively unobtrusive location. The implosion cartridge 46 of FIG. 2 may be used in the apparatus configuration of FIG. 4, however, there is shown in FIG. 5 a modified version of the implosion cartridge that function equally as well.

Figure 5:
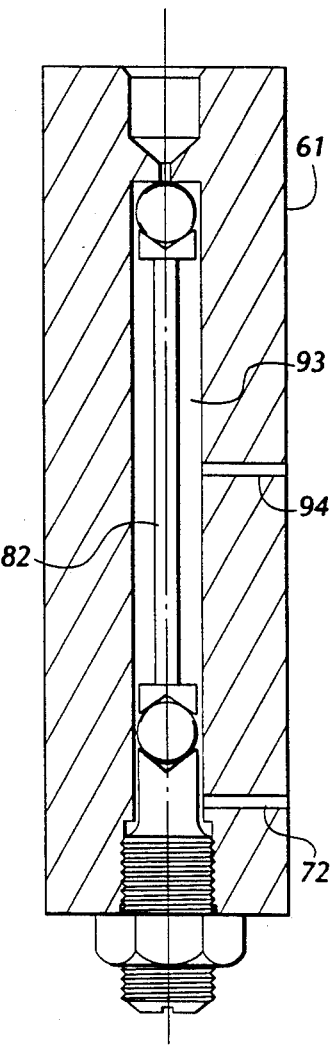
FIG. 5 is an elevation, cross-sectional view of a second implosion cartridge of the present invention.

In FIG. 5, where, for simplicity, like parts have been given the same reference numerals as in FIG. 2, housing 61 has a single elongated chamber 93 therein of a diameter which is selectively sized to restrain the buckling of column 82 beyond its elastic limit, identically in this respect to the function of ringed side wall 64. Housing 61 has, in addition to the purging channel or conduit 72, a second purging channel 94. With this arrangement, compressed air from air compressor 56 may be introduced through conduit 94 into chamber 93, and water drained off through conduit 72, thereby eliminating the necessity for a plurality of valves.

The operation of the apparatus of FIGS. 4 and 5 is substantially the same as that of the apparatus of FIGS. 1 and 2.

Figure 6:
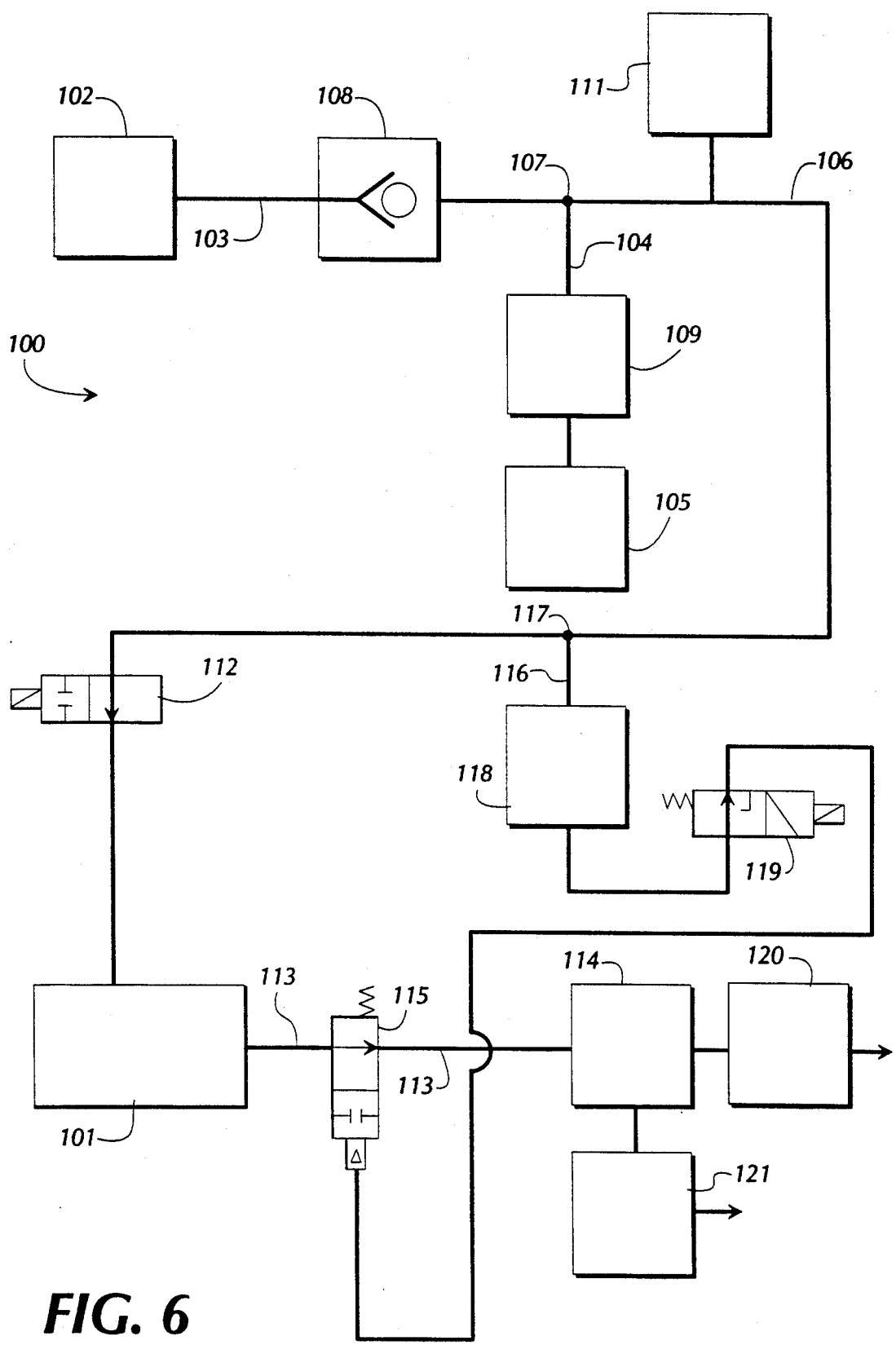
FIG. 6 is a block diagram depiction of a third embodiment of the present invention.

FIG. 6 diagrammatically illustrates a third embodiment of the invention in which air, rather than liquid, is the medium for compression and explosive decompression of the atmosphere around the tools or instruments being sterilized. FIG. 6 depicts sterilization apparatus 100 which comprises a housing 101 defining therein a pressure chamber (not shown) in which the articles to be sterilized are placed. The housing 101 can take the form of virtually any suitable housing well known in the art, an example of which is further described in reference to FIG. 7, and which is capable of safely containing at least three Kpsi air pressures therein. An air compressor 102 supplies filtered, oilless, compressed air through suitable pressure lines or conduits 103 and 104 to a compressed air storage tank 105. As shown in FIG. 6, pressure conduit 106 joins conduits 103 and 104 at a "T"-shaped conduit junction 107. Conduit 106 thereafter connects to housing 101. Positioned between air pump 102 and junction 107 in conduit 103 is check valve 108. Valve 108 is a one way valve which permits air flow therethrough from air compressor 102 to conduit 104 or conduit 106, but will not permit the reverse flow of air back to pump 102. Positioned in conduit 104 between junction 107 and air storage tank 105 is valve 109 which controls air flow to and from air storage tank 105 to the remaining, accessible elements of sterilization apparatus 100. Positioned in pressure conduit 106 is a pressure gauge or transducer 111 to monitor and display pressure. Also mounted in pressure conduit 106 is a solenoid operated air valve 112. Valve 112 either is selectively opened to allow passage of compressed air into the pressure chamber of housing 101, or conversely is closed either to prevent air flow into chamber 101 or out of chamber 101 back through conduit 106 towards air pump 102.

Conduit 113 also is connected to housing 101, and is intended to allow the pressurized air within the chamber of housing 101 to be nearly instantaneously exhausted from the pressure chamber of housing 101. Conduit 113 connects the pressure chamber of housing 101 to an air pressure surge tank 114. Positioned within conduit 113 between housing 101 and surge tank 114 is a quick opening, piston actuated valve 115. Valve 115 is designed to open so quickly as to allow the nearly instantaneous decompression or depressurization of the atmosphere within the pressure chamber of housing 101. Quick opening valve 115, for example, can be an air operated, piston valve of the type manufactured by the Autoclave Engineers Group of Erie, Pa. Other known, quick opening valves will suffice. The air pressure needed to operate valve 115 is taken from conduit 106 via conduit 116, which joins conduit 106 between solenoid valve 112 and junction 107, at junction 117. The purpose of conduit 116 is to supply operating air pressure to quick opening valve 115. Pressure reducing valve 118 is positioned in conduit 116 between junction 117 and valve 115 to reduce the operating air pressure delivered to valve 115.

When the system is operational, as discussed below, pressure reducing valve 118 normally reduces the air pressure within conduit 116 from approximately 3 Kpsi to approximately 100 psi, the operating air pressure needed to control quick opening valve 115. A solenoid valve 119 is positioned in conduit 116 between pressure reducing valve 118 and quick opening valve 115 to control the flow of air pressure to valve 115. A muffler 120 is connected to surge tank 114 to muffle the sound of the compressed air explosively released from the pressure chamber of housing 101 into surge tank 114. Also connected to the lowermost portion of surge tank 114 is a drain valve 121 which is utilized to drain any moisture collected in surge tank 114 from the operation of sterilization apparatus 100.

It should be recognized that all of the above-referenced components which comprise the third embodiment of the present invention are well known, easily attainable, "off the shelf" components readily assembled by one skilled in the art by following the present disclosure. The pressure valves, including quick opening, high pressure valve 115, fluid pressure reducers, gauges and high pressure conduits can be obtained, for example, from the Autoclave Engineers Group of Erie, Pa. The high pressure fittings such as the pressure junctions or "union tees" 107 and 117 can be obtained, for example, from the Sno-Trik Company of Solon, Ohio. The remaining elements are readily obtained from these or other companies. Additionally, other ways of applying controlled air pressurization to a housing such as housing 101, and a controlled depressurization of housing 101 exist, using known components. The above arrangement of components to accomplish this purpose is made for illustrative purposes only, and is not intended in any way to limit the present invention to this exact arrangement.

The pressure housing 101 also is readily obtainable, and need only include a housing which defines a chamber into which the tools or instruments for sterilization may be inserted and removed. The housing must be capable of safely maintaining pressure of approximately 3 Kpsi and include the appropriate fittings to allow the chamber within the housing to be pressurized and then rapidly or nearly instantaneously depressurized. For example, in FIG. 7 there is shown a pressure housing arrangement for use in the embodiment of FIG. 6. Housing 101 can be of an elongated cylindrical shape, and defines therein a chamber 152 extending therethrough, a first enlarged bore 153 at one end of housing 101 and a second enlarged bore 154 at the opposite end of housing 101. Bore 153 has a tapered sealing surface 156 adjacent chamber 152, and, in like manner, bore 154 has a tapered sealing surface 157 adjacent chamber 152. Housing 101 is shown with a basket 158 disposed in chamber 152, which contains the tools or instruments to be sterilized.

A sealing plug 159, having an outer diameter dimensioned to be an easy slip fit into bore 153, has a tapered end surface 161 which matches the taper end surface 156 of bore 153. A sealing ring 162 is mounted on tapered surface 161, although it could be, for example, mounted on tapered surface 156. Plug 159 has a lateral bore 163 extending therethrough which is adapted to match corresponding bores 164 and 166 in housing 101. Bores 163, 164, and 166 are adapted to receive a locking pin 167 in a slip fit manner when they are properly aligned, with sealing ring 162 thereby compressed between surfaces 156 and 161, sealing and locking one end of housing 101. Plug 159 is equipped with a handle 168 to facilitate insertion and removal of plug 159. At the other end of housing 101 and hence chamber 152 is a second plug 169 having a tapered surface 171 to which is mounted a sealing ring or gasket 172 and which matches tapered surface 157. Plug 169 defines a bore 173 passing axially therethrough and a threaded fitting 174 for coupling to conduit 113. Plug 169 has a shoulder 176 formed thereon against which a threaded locking member 177 bears. The threads 178 on locking member 177 mate with corresponding threads 179 defined by the side wall of bore 154 so that member 177 can be screwed into bore 154 to bear against shoulder 176 and thereby compress sealing ring 172 and seal the other or second end of housing 101 and hence chamber 152. Locking member 177 has a handle 181 to facilitate screwing it in and out, and also has air passages 182 and 183 for bleeding off any remanent pressurized air in chamber 152 when the seal at ring 172 is broken.

Housing 101 also includes fitting 185 and running through in its side wall between plugs 159 and 169. Fitting 185 connects to inlet pressure conduit 106 to allow chamber 152 to be pressurized by air passing through conduit 106 from valve 112.

In operation, pin 167 is pulled from bores 163, 164 and 166, allowing plug 159 to be separated from housing 101, thereby breaking the airtight seal accomplished by sealing ring 162. A basket, preferably made of woven wire stainless steel or perforated stainless steel sheets, containing the tools or instruments to be sterilized is placed within chamber 152. As discussed above in reference to the prior embodiments, solid non-porous articles such as stainless steel balls can be added to the tools in stainless steel basket 158 in order to decrease the amount of volume within chamber 152 which must be pressurized. Plug 159 is refitted onto housing 101, and locking pin 167 is inserted to insure that plug 159 is properly locked onto housing 101, effectively sealing chamber 152. Pump or air compressor 102 delivers compressed air through lines 103 and 106 to pressurize chamber 152 to, for example, 3 Kpsi. In the pressurization, valve 109 is open, allowing air storage tank 105 also to be pressurized. Valve 112 also is open, allowing chamber 152 also to be pressurized to 3 Kpsi. Once chamber 152 is pressurized, solenoid valve 112 is closed. Since quick opening valve 115 is in its closed position at this point, it is readily understood that chamber 152 is held at the desired pressure. The pressure in chamber 152 is held for a predetermined "soaking" period of time, subjecting the microbes or microorganisms contaminating the tools to be sterilized to this pressure for the selected interval.

As previously discussed, pressure conduit 116 taps off of conduit 106 to provide a pilot operating pressure to quick opening valve 115. Because the pressure to operate valve 115 need not be at the system operating pressure of, for example, 3 Kpsi, a pressure reducing valve 118 is disposed within conduit 116 to reduce the pilot operating air pressure delivered to valve 115 to, for example, 100 psi.

After the tools are subjected to the selected pressure within chamber 152 for the desired interval, quick opening valve 115 is opened to allow a nearly instantaneous decompression of chamber 115. This decompression occurs in approximately 1 to 10 milliseconds. The forceful exhaustion of the pressurized air in chamber 152 is nearly instantaneously delivered to surge tank 114. Tank 114 defines a chamber sufficiently larger than chamber 152 to allow for the expansion of the air exhausted from chamber 152. When this exhaustion of the air occurs, a high decibel sound is thereby created. To muffle this sound, muffler 120 is connected to surge tank 114, and the air exhausted into surge tank 114 is allowed to escape to the atmosphere from muffler 120. Drain valve 121 is connected to the lowermost portion of surge tank 114 to allow for the gravitational drainage of any moisture which collects in tank 114 from the above-described process.

The pressurization of the tools, and therefore the microorganism contaminants on the tools, and their nearly instantaneous decompression stresses the microorganism to the point of deactivation. This basic process is the identical process to that described above in reference to the prior embodiment, that is high compression and rapid decompression of the microorganisms. Also as described in reference to the prior embodiments, repetitive cycles of high compression and nearly instantaneous decompression can be accomplished to repetitively stress the organisms to facilitate their deactivation. The pressure/time curve for this embodiment also is shown in FIG. 3, with reference to the "air/gas" variable along the graph's y-axis. The characteristics of the curve for this embodiment essentially will be the same as in the prior embodiments.

The invention as described relative to the various embodiments illustrated in the figures subjects the material or tools to be sterilized to both compression and explosive decompression sterilization. The invention works equally well with either packaged or unpackaged materials, where the package is sufficiently flexible to transmit the pressure to the materials or tools, and does not require elevated temperatures, steam, chemicals, or sporicidal atmospheres to achieve sterilization.

The foregoing has been for purposes of illustrating the principles of the invention and the numerous features thereof. Various modifications and changes may be made by workers skilled in the art without departure from the spirit and scope of the invention.

We claim:

1. A method for sterilizing materials and/or objects comprising:
    placing the materials or objects to be sterilized in a pressure chamber;
    introducing a fluid under pressure into the pressure chamber to subject the material or objects to a pressure of at least one thousand pounds per square inch; and
    explosively decompressing the pressure in the chamber when the pressure therein reaches a predetermined maximum pressure.

2. The method for sterilizing materials and/or objects as claimed in claim 1 wherein the fluid used is water.

3. The method for sterilizing materials and/or objects as claimed in claim 1 wherein the fluid used is air.

4. The method for sterilizing materials and/or objects as claimed in claim 1 and further including the step of applying the pressurized fluid in the pressure chamber to a pressure sensitive valve member having an outlet passage.

5. The method for sterilizing materials and/or objects as claimed in claim 4 wherein the step of explosively decompressing the pressure in the chamber comprises opening the outlet passage and passing the fluid under pressure from the pressure chamber to the pressure sensitive valve member and through the outlet passage.

6. The method for sterilizing materials and/or objects as claimed in claim 5 and further including the steps of passing the fluid under pressure to an accumulation chamber in the pressure sensitive valve member, and subsequently purging the accumulation chamber of the pressure sensitive valve member of accumulated fluid.

7. The method for sterilizing materials and/or objects as claimed in claim 6 wherein the step of purging the accumulation chamber of the pressure sensitive valve member comprises introducing air under pressure into the accumulation chamber.

8. A sterilization apparatus comprising:
    a housing member having a chamber therein for containing material or objects to be sterilized;
    first means in communication with said chamber for introducing a fluid under pressure into said chamber to pressurize said chamber to at least one thousand PSI;
    second means in communication with said chamber having an opening therein for exhausting pressurized fluid from said chamber, said second means including pressure sensitive means for sealing said opening; and
    means for producing an explosive decompression of said chamber by unsealing said opening;
    whereby fluid under pressure in said chamber exits said chamber through said opening.

9. A sterilization apparatus as claimed in claim 8 wherein said first means comprises a valve member having an inlet opening, an outlet opening, and an exhaust opening, said outlet opening being in communication with said chamber and said inlet opening being in communication with a source of fluid under pressure.

10. A sterilization apparatus as claimed in claim 9 wherein said first means further comprises actuatable means for preventing fluid under pressure from passing through said inlet opening to said outlet opening.

11. A sterilization apparatus as claimed in claim 10 wherein said means for producing an explosive decompression comprises means for actuating said actuatable means to block the pressurized fluid from passing through said outlet opening.

12. A sterilization apparatus as claimed in claim 8 wherein said second means has an input opening, an output opening, and an exhaust opening, said input opening being in fluid communication with said first means and said output opening being in fluid communication with said chamber.

13. A sterilization apparatus as claimed in claim 12 wherein said pressure sensitive means has a first sealing position whereby said exhaust opening is sealed and a second sealing position whereby said input opening is sealed.

14. A sterilization apparatus comprising:
    a housing member having a chamber therein for containing material or objects to be sterilized;
    an implosion cartridge member in communication with said chamber through an inlet passage in said cartridge and having means for sealing said inlet passage;
    means for introducing a liquid under pressure into said chamber to pressurize said chamber;
    said cartridge member having means responsive to the pressure in said chamber for explosively decompressing said chamber when the pressure therein reaches a predetermined maximum by unsealing said inlet passage.

15. A sterilization apparatus as claimed in claim 14 and further comprising means in said housing for pressure sealing said chamber.

16. A sterilization apparatus as claimed in claim 14 wherein said means for sealing said inlet passage comprises means movable toward and away from said inlet passage under control of said means responsive to the pressure in said chamber.

17. A sterilization apparatus as claimed in claim 14 and further comprising a conduit extending from said chamber to the exterior of said housing.

18. A sterilization apparatus as claimed in claim 17 wherein said inlet passage of said cartridge member is connected to said conduit.

19. A sterilization apparatus comprising:
    a housing member having a first chamber therein;
    means for delivering a fluid under a pressure of at least one thousand pounds per square inch to said chamber;
    pressure sensitive means having a second chamber therein in fluid communication with said first chamber through an inlet passage;
    said pressure sensitive means having sealing means for sealing said inlet passage;
    and means for depressurizing explosively a fluid in said first chamber comprising means for causing fluid under pressure to flow past said sealing means into said second chamber when the pressure in said first chamber reaches a predetermined maximum.

20. A sterilization apparatus as claimed in claim 19 and further comprising a relief valve member in fluid communication with said first chamber.

21. A sterilization apparatus as claimed in claim 19 and further comprising means for purging said second chamber of accumulated fluid.

22. A sterilization apparatus as claimed in claim 21 wherein said means for purging comprises an air compressor in fluid communication with said second chamber.

23. A pressure sensitive valve member for use with a pressurized apparatus comprising:
a housing having a chamber therein;
inlet means for transmitting fluid under pressure from the exterior of said housing into said chamber;
means for sealing said inlet means;
pressure sensitive means for maintaining said means for sealing in an inlet sealing position, said pressure sensitive means having a critical buckling load factor and constructed and arranged to buckle when pressure on said means for sealing exceeds said critical buckling load factor;
whereby fluid under pressure flows from the exterior of the housing into said chamber when the pressure of said fluid exceeds said critical buckling load factor.

24. A pressure sensitive valve member as claimed in claim 23 wherein said pressure sensitive means comprises an elongated columnar member having first and second ends, said first end constructed and arranged to bear against said means for sealing said inlet.

25. A pressure sensitive valve member as claimed in claim 23 and further comprising an adjusting member in said housing, said second end of said columnar member constructed and arranged to bear against said adjusting member.

26. A pressure sensitive valve means as claimed in claim 23 and further comprises conduit means in said housing connecting said chamber to the exterior of said housing.

27. A pressure actuated valve comprising:
a housing having an elongated chamber therein;
an opening in said housing extending between the exterior of said housing and said chamber, said opening including means defining a valve seat;
a sealing member constructed and arranged to bear against said valve seat;
pressure sensitive means having first and second ends for maintaining said sealing member against said valve seat, said pressure sensitive means having a pressure load buckling factor,
whereby when said load buckling factor is reached said pressure sensitive means buckles and said sealing member moves off of said valve seat.

28. A pressure actuated valve as claimed in claim 27 wherein said sealing member is a spherical member.

29. A pressure actuated valve as claimed in claim 28 wherein said first end of said pressure sensitive member has a retainer member having a conical recess therein constructed and arranged to bear against said spherical member.

30. A pressure actuated valve as claimed in claim 27 wherein said pressure sensitive member comprises an elongated columnar member extending through said chamber.

31. A pressure actuated valve as claimed in claim 27 and further comprising an adjustable support member within said housing having a first end adjacent said second end of said pressure sensitive means.

32. A pressure actuated valve as claimed in claim 31 wherein first end of said support member has a cone shaped recess therein.

33. A pressure actuated valve as claimed 32 wherein said second end of said pressure sensitive means has a retainer member mounted thereon.

34. A pressure actuated valve as claimed in claim 33 wherein said retainer member has a cone shaped recess therein.

35. A pressure actuated valve as claimed in claim 34 and further comprising a spherical member between said retainer and said first end of said support member and constructed and arranged to bear against said cone shaped recesses.

* * * * *